(12) United States Patent
Matsuda et al.

(10) Patent No.: US 8,664,355 B2
(45) Date of Patent: Mar. 4, 2014

(54) CELL-FREE PROTEIN SYNTHESIS METHOD WITH THE USE OF LINEAR TEMPLATE DNA AND CELL EXTRACT THEREFOR

(75) Inventors: Natsuko Matsuda, Yokohama (JP); Takanori Kigawa, Yokohama (JP); Shigeyuki Yokoyama, Yokohama (JP)

(73) Assignee: Riken, Saitama (JP)

( * ) Notice: Subject to any disclaimer, the term of this patent is extended or adjusted under 35 U.S.C. 154(b) by 420 days.

(21) Appl. No.: 11/798,877

(22) Filed: May 17, 2007

(65) Prior Publication Data

US 2008/0032329 A1 Feb. 7, 2008

Related U.S. Application Data

(63) Continuation of application No. PCT/JP2005/021265, filed on Nov. 18, 2005.

(30) Foreign Application Priority Data

Nov. 19, 2004 (JP) ................................. 2004-335514

(51) Int. Cl.
```
A61K 38/00      (2006.01)
C07K 5/00       (2006.01)
C07K 7/00       (2006.01)
C12Q 1/68       (2006.01)
C12P 19/34      (2006.01)
```
(52) U.S. Cl.
USPC ........................... 530/333; 435/6.1; 435/6.12

(58) Field of Classification Search
None
See application file for complete search history.

(56) References Cited

U.S. PATENT DOCUMENTS

| | | | |
|---|---|---|---|
| 5,264,341 | A | 11/1993 | Maciak et al. |
| 5,270,181 | A | 12/1993 | McCoy et al. |
| 5,532,151 | A | 7/1996 | Chantry et al. |
| 5,674,729 | A | 10/1997 | Wimmer et al. |
| 5,800,984 | A | 9/1998 | Vary |
| 5,804,374 | A | 9/1998 | Baltimore et al. |
| 5,869,286 | A | 2/1999 | Yao et al. |
| 5,959,085 | A | 9/1999 | Garrone et al. |
| 5,962,246 | A | 10/1999 | Ladner et al. |
| 6,136,568 | A | 10/2000 | Hiatt et al. |
| 6,303,337 | B1 | 10/2001 | Rothschild et al. |
| 6,511,832 | B1 | 1/2003 | Guarino et al. |
| 6,780,607 | B2 | 8/2004 | Choi et al. |
| 7,195,895 | B2 | 3/2007 | Motoda et al. |
| 7,348,134 | B2 | 3/2008 | Lingappa et al. |
| 2002/0025525 | A1 | 2/2002 | Shuber |
| 2002/0142387 | A1 | 10/2002 | Seki et al. |
| 2003/0050453 | A1 | 3/2003 | Sorge |
| 2004/0121346 | A1 | 6/2004 | Endo et al. |
| 2004/0137448 | A1 | 7/2004 | Thornton et al. |
| 2005/0095705 | A1 | 5/2005 | Kadan et al. |
| 2005/0244920 | A1 | 11/2005 | Shirouzu et al. |
| 2007/0281337 | A1 | 12/2007 | Imataka et al. |

FOREIGN PATENT DOCUMENTS

| | | |
|---|---|---|
| EP | 0469610 A1 | 2/1992 |
| EP | 1143009 A1 | 10/2001 |
| EP | 1 176 210 A1 | 1/2002 |
| EP | 1 316 616 A1 | 6/2003 |
| EP | 1354959 A1 | 10/2003 |
| EP | 1655375 A1 | 5/2006 |
| EP | 1857558 A1 | 11/2007 |
| JP | 4-200390 A | 7/1992 |
| JP | 7-110236 A | 4/1995 |
| JP | 9-107954 A | 4/1997 |
| JP | 9-234074 A | 9/1997 |
| JP | 2000-175695 A | 6/2000 |
| JP | 2000-325076 A | 11/2000 |
| JP | 2002-238595 A | 8/2002 |
| JP | 2003-18999 A | 1/2003 |
| JP | 2003-235598 A | 8/2003 |
| JP | 2004-91790 A | 3/2004 |
| JP | 2004-215651 A | 8/2004 |
| JP | 2004-267205 A | 9/2004 |
| JP | 2004-290181 A | 10/2004 |
| JP | 2005006646 A | 1/2005 |
| JP | 2005-225796 A | 8/2005 |
| WO | WO 88/08453 | 11/1988 |
| WO | WO-88/08453 A1 | 11/1988 |
| WO | WO-92/07949 A1 | 5/1992 |
| WO | WO-92/11390 A1 | 7/1992 |

(Continued)

OTHER PUBLICATIONS

Ha et al., "Immunostimulation with *Escherichia coli* extract: prevention of recurrent urinary tract infections," International Journal of Antimicrobial Agents, 2008, vol. 31S, pp. S63-S67.*

Kim et al., "A highly efficient cell-free protein synthesis system from *Escherichia coli*," European Journal of Biochemistry, 1996, vol. 239, pp. 881-886.*

Kigawa et al., "Preparation of *Escherichia coli* cell extract for highly productive cell-free protein expression," Journal of Structural and Functional Genomics, Mar. 2004, vol. 5, pp. 63-68.*

(Continued)

*Primary Examiner* — Young J Kim
(74) *Attorney, Agent, or Firm* — Birch, Stewart, Kolasch & Birch, LLP (57) ABSTRACT

It is provided a simple and efficient process for producing a large amount of protein in a cell-free protein synthesis system, through a continuous synthesis reaction over a long time using a linear DNA as a template. The continuous synthesis reaction is carried out for at least one hour with a cell-free protein synthesis system comprising an extract of *Escherichia coli* cells cultured at any temperature between 18° C. and 36° C., and a linear template DNA encoding the protein. The continuous protein synthesis system is preferably a dialysis system or a continuous flow system. The cell-free protein synthesis system by dialysis system comprises an internal dialysate comprising the extract and the linear template DNA, an external dialysate comprising a substrate solution for protein synthesis, and a dialysis membrane through which the substrate can be transferred.

11 Claims, 3 Drawing Sheets

(56) References Cited

FOREIGN PATENT DOCUMENTS

| WO | WO-92/13955 A1 | 8/1992 |
|---|---|---|
| WO | WO-97/46696 A1 | 12/1997 |
| WO | WO-99/02671 A1 | 1/1999 |
| WO | WO-99/14370 A1 | 3/1999 |
| WO | WO-99/20798 A1 | 4/1999 |
| WO | WO-99/57992 A1 | 11/1999 |
| WO | WO-00/56914 A1 | 9/2000 |
| WO | WO-01/83805 A2 | 11/2001 |
| WO | WO-01-83805 A2 | 11/2001 |
| WO | WO-02/18586 A1 | 3/2002 |
| WO | WO-02/090537 A1 | 11/2002 |
| WO | WO-03/097829 A1 | 11/2003 |

OTHER PUBLICATIONS

Sitaraman et al., "A novel cell-free protein synthesis system," Journal of Biotechnology, Jun. 2004, vol. 110, pp. 257-263.*
Sawasaki et al., "A cell-free protein synthesis system for high-throughput proteomics," PNAS, Nov. 2002, vol. 99, No. 23, pp. 14652-14657.*
Giuliodori et.al, "Preferential translation of cold-shock mRNSs during cold adaptation". RNA (2004), pp. 10:265-276.
Nishimura et al. "Cell-Free System Derived from Heat-Shocked *Escherichia coli*:: Synthesis of Enzyme Protein Possessing Higher Specific Activity". Journal of Fermentation and BioEngineering vol. 79, No. 2 pp. 131-135. (1995).
Yu et al. "An efficient recombination sustem for chromosome engineering in *Escherichia coli*" pp. 5978-5983 ,PNAS ,May 23, 2000, vol. 97, No. 11.
Pain, Methods in Molecular Biology, vol. 77: Protein Synthesis: Methods and Protocols, "Analysis of Translational Activitiy of Extracts Derived from Oocytes and Eggs of *Xenopus laevis*," Ed. R. Martin, Humana Press, Towata, NJ, 1998.
Rowen et al., NCBI Protein AAF 02829, Submitted (Apr. 25, 1999) Multimegabase Sequenceing Center, University of Washington.
Zubay, "In Vitro Synthesis of Protein in Microbial Systems," Annual Review of Genetics, 1973, vol. 7, pp. 267-287.
Pratt et al., "Identification of gene products by restriction endonuclease DNA fragments using an *E. coli* in vitro system," Nucleic Acids Research (1981) vol. 9, No. 19, pp. 4459-4474.
Benzinger et al., "Transfection of *Escherichia coli* Spheroplasts, V. Activity of recBC Nuclease in Rec+ and Rec- Spheroplasts Measured with Different Forms of Bacteriophage DNA," Journal of Virology (Apr. 1975), vol. 15, No. 4, pp. 861-871.
Lorenz et al., "Bacterial Gene Transfer by Natural Genetic Transformation in the Environment" (Sep. 1994) vol. 58, No. 3, pp. 563-602.
Yang et al., "Cell-free coupled transcription-translation system for investigation of linear DNA segments," Proc. Natl. Acad. Sci. USA (Dec. 1980), vol. 77, No. 12, pp. 7029-7033.
Walter et al., "Preparation of Microsomal Membranes for Cotranslation Protein Translocation", Methods in Enzymology, vol. 96, pp. 87-93, 1983.
Broeze, R. J., et al., "Effects of Low Temperature on In Vivo and In Vitro Protein Synthesis in *Escherichia coli* and *Pseudomonas fluorescens*," J. Bacteriology, vol. 134, No. 3, pp. 861-874 (1978).
Wieder K. J. et al., Proceedings of the National Academy of Sciences of USA, 1982, vol. 79, pp. 3599-3603.
Abstract of Mikami S. et al., Protein Expression and Purification, Oct. 25, 2005.
Sawasaki T. et al., Protein, Nucleic Acid and Enzyme, 2004, vol. 49, pp. 1514-1519.
Giller et al., "A homologous in vitro system to analyze transcription of a mouse immunoglobulin u heavg-chain gene", Eur. J. Biochem., vol. 172, pp. 679-685, 1988.
Nishimura et al., "Enhancement of Protein Synthesis in Continuous-Flow, Cell-Free System by Improvement of Membrane Permeation", Journal of Fermentation and Bioengineering, vol. 80, No. 4, pp. 403-405, 1995.

Bochkareva et al., "Chaperonin-promoted Post-translational Membrane Insertion of a Multispanning Membrane Protein Lactose Permease", Journal of Biological Chemistry, vol. 271, No. 36, pp. 22256-22261, 1996.
Wheatley et al., "Glycosylation of G-protein-coupled receptors for hormones central to normal reproductive functioning: its occurrence and role", Human Reproduction Update, vol. 5, No. 4, pp. 356-364, 1999.
Kigawa et al., "Cell-free production and stable-isotope labeling of milligram quantities of proteins", FEBS Letters, vol. 442, pp. 15-19, 1999.
Booth et al., Biochemical Society Transactions, vol. 28, Part 3, p. A50, 2000.
Kigawa et al., "High-throughput Cell-free Protein Expression System for Structural Proteomics", Protein, Nucleic Acid and Enzyme, vol. 47, No. 8, pp. 1014-1019, 2002 (with full English Translation).
Kain et al., "Universal Promoter for Gene Expression Without Cloning: Expression-PCR", BioTechniques, vol. 10, No. 3, pp. 366-368 and 370, 1991, XP000912135.
MacFerrin at al., "Overproduction and dissection of proteins by the expression-cassette polymerase chain reaction", Proc. Natl. Acad. Sci., vol. 87, No. 5, pp. 1937-1941, 1990, XP000268593.
Ohuchi et al., "In vitro method for the generation of protein libraries using PCR amplification of a single DNA molecule and coupled transcription/translation", Nucleic Acids Research, vol. 26, No. 19, pp. 4339-4346, 1998, XP002119037.
Nakano et al., "Efficient Coupled Transcription/Translation from PCR Template by a Hollow-Fiber Membrane Bioreactor", Biotechnology and Bioengineering, vol. 64, No. 2, pp. 194-199, XP001084028, (1991).
Sandhu et al., "Dual Asymmetric PCR: One-Step Construction of Synthetic Genes", BioTechniques, vol. 12, No. 1, pp. 14-16, 1992, XP002134139.
Horton et al., "Engineering hybrid genes without the use of restriction enzymes: gene splicing by overlap extension", Gene, vol. 77, pp. 61-68, 1989, XP002090392.
Liu et al., "Functional characterization of novel human ARFGAP3", FEBS Letters, vol. 490, Nos. 1-2, pp. 79-83, 2001.
Laage et al., "Strategies for Prokaryotic Expression of Eukaryotic Membrane Proteins", Traffic, vol. 2, No. 2, pp. 99-104, 2001.
Yoshida et al., "In Vitro Synthesis of Hyaluronan by a Single Protein Derived from Mouse HAS1 Gene and Characterization of Amino Acid Residues Essential for the Activity", Journal of Biological Chemistry, vol. 275, No. 1, pp. 497-506, 2000.
Lehto et al., "Release of the glycosylphosphatidylinositol-anchored enzyme ecto-5'-nucleotidase by phospholipase C: catalytic activation and modulation by the lipid bilayer", Biochem. Journal, vol. 332, pp. 101-109, 1998.
The pET Expression System, http://www.bio.davidson.edu/Course/Molbio?nolStudents/spring2003/Causey/p- ET.html, pp. 1-4, 2003.
Tucker et al., "Purification of a rat neurotensin receptor expressed in *Escherichia coli*", Biochem. Journal, vol. 317, pp. 891-899, 1996.
Grisshammer et al., "Expression of a rat neurotensin receptor in *Escherichia coli*", Biochem. Journal, vol. 295, pp. 571-576, 1993.
Abdulaev et al., "Functionally Discrete Mimics of Light-activated Rhodopsin Identified through Expression of Soluble Cytoplasmic Domains", Journal of Biological Chemistry, vol. 275, No. 50, pp. 39354-39363, 2000.
Sachdev et al., "Solubility of Proteins Isolated from Inclusion Bodies is Enhanced by Fusion to Maltose-Binding Protein or Thioredoxin", Protein Expression and Purification, vol. 12, No. 1, pp. 122-132, 1998.
McIntyre et al., "Procathepsins L and D are Membrane-Bound in Acidic Microsomal Vesicles", Journal of Biological Chemistry, vol. 266, No. 23, pp. 15438-15445, 1991.
Invitrogen, "Flexible in vitro expression with high-yield results", Expressions, vol. 9, Issue 2, p. 7, 2002.
Novagen, "pET-23a-d(+) Vectors", p. 1, 1998.
Falk, "Cell-free synthesis and assembly of connexins into functional gap junction membrane channels", EMBO Journal, vol. 16, No. 10, pp. 2703-2716, 1997.

(56) References Cited

OTHER PUBLICATIONS

Rhee et al., "Channel-Forming Activity of Immunoaffinity-Purified Connexin32 in Single Phospholipid Membranes", Biochemistry, vol. 35, No. 28, pp. 9212-9223, 1996.
Ohtaki et al., "Expression, Purification, and Reconstitution of Receptor for Pituitary Adenylate Cyclase-activating Polypeptide", Journal of Biological Chemistry, vol. 273, No. 5, 15464-15473, 1998.
Mambetisaeva et al., "Expression of Three Functional Domains of Connexin 32 as Thioredoxin Fusion Proteins in *Escherichia coli* and Generation of Antibodies", Protein Expression and Purification, vol. 11, No. 1, pp. 26-34, 1997.
Peng et al., "Cystic fibrosis transmembrane conductance regulator; expression and helicity of a double membrane-spanning segment", FEBS Letters, vol. 413, No. 1, pp. 29-33, 1998.
Potapov et al., "Correlation between poly(U) misreading and poly(dT) translation efficiency in *E coli* cell-free systems", Biochimie, vol. 72, pp. 345-349, 1990.
Okamoto-Hosoya et al., "An aberrant protein synthesis activity is linked with antibiotic overproduction in *rpsL* mutants of *Streptomyces coelicolor* A3(2)", Microbiology, Vol, 149, pp. 3299-3309, 2003.
Hu et al., "Novel Approach for Improving the Productivity of Antibiotic-Producing Strains by Inducing Combined Resistant Mutations", Applied and Environmental Microbiology, pp. 1885-1892, 2001.
Hosoya et al., "Acquisition of Certain Streptomycin-Resistant (str) Mutations Enhances Antibiotic Production in Bacteria", Antimicrobial Agents and Chemotherapy, vol. 42, pp. 2041-2047, 1998.
Chumpolkulwong et al., "Effects of *Escherichia coli* ribosomal protein S12 mutations on cell-free protein synthesis", Eur. J. Biochem., vol. 271, pp. 1127-1134, 2004.
Hwang, Y.-I., "Mutant 30S ribosomal subunit S12", Database EMBL, Oct. 1, 2002, XP-002353555.
Office Action mailed Jan. 13, 2009 in Japanese Application No. 2002-345597.
Inaoka et al., "Construction of an In Vivo Nonsense Readthrough Assay System and Functional Analysis of Ribosomal Proteins S12, S4, and 8S in *Bacillus subtilis*", Journal of Bacteriology, vol. 183, No. 17, pp. 4958-4963, 2001.
Funatsu et al., "Ribosomal Proteins; Location of Amino-acid Replacements in Protein S12 isolated from *Escherichia coli* Mutants Resistant to Streptomycin", J. Mol. Biol., vol. 68, pp. 547-550, 1972.
Timms et al., "Mutant sequences in the *rpsL* gene of *Escherichia coli* B/r: mechanistic implications for spontaneous and ultraviolet light mutagenesis", Molecular and General Genetics, vol. 232, pp. 89-96, 1992.
Shehata et al., "Effect of Temperature on the Size of *Escherichia coli* Cells", Journal of Bacteriology, vol. 124, No. 2, pp. 857-862, 1975.
Patterson et al., "Deductive Analysis of a Protein-Synthesis Mutant of *Escherichia coli*", Biochemical Genetics, vol. 8, No. 2, pp. 205-230, 1973.
Klammt et al., "Cell-Free Production of Integral Membrane Proteins on a Preparative Scale", Methods in Molecular Biology, vol. 375, pp. 57-78, 2007.
Mathews et al., "Mammalian Cell-Free Protein Synthesis Directed by Viral Ribonucleic Acid", Eur. J. Biochem. vol. 17, pp. 328-338, 1970.
Zawada et al., "Effects of Genotype and Growth Conditions on Cell-Free Protein Synthesis Systems", Abstracts of Papers of the American Chemical Society, vol. 224, Nos. 1-2, p. BIOT 91, 2002, XP009068071.
Jones et al., "Function of a Relaxed-Like State following Temperature Downshifts in *Escherichia coli*", Journal of Bacteriology, vol. 174, No. 12, pp. 3903-3914, 1992.
Wang et al., "An Optimized Yeast Cell-Free System: Sufficient for Translation of Human Papillomavirus 58 L1 mRNA and Assembly of Virus-like Particles", Journal of Bioscience and Bioengineering, vol. 106, No. 1, pp. 8-15, 2008.
Hofbauer et al., "Preparation of a mRNA-Dependent Cell-Free Translation System from Whole Cells of *Saccharomyces cerevisiae*", Eur, J. Biochem. vol. 122, pp. 199-203, 1982.

Kim et al., "Expression-independent consumption of substrates in cell-free expression system from *Escherichia coli*", Journal of Biotechnology, vol. 84. pp. 27-32, 2000.
Kim et al., "Continuous Cell-Free Protein Synthesis Using Glycolytic Intermediates as Energy Sources", J. Microbiol. Biotechnol., vol. 18, No. 5, pp. 885-888, 2008.
Ertola et al., "Design, Formulation, and Optimization of Media", Bioprocess Technol., vol. 21, pp. 89-137, 1995.
Lee et al., "Statistical Medium Formulation and Process Modeling by Mixture Design of Experiment for Peptide Overexpression in Recombinant *Escherichia coli*", Applied Biochemistry and Biotechnology, vol. 135, pp. 81-100, 2006.
Carroll et al., "Preparation of a Cell-Free Translation System with Minimal Loss of Initiation Factor eIF-2/eIF-2B Activity", Analytical Biochemistry, vol. 212, pp. 17-23, 1993.
Henis-Korenblit et al., "The caspase-cleaved DAP5 protein supports internal ribosome entry site-mediated translation of death proteins", PNAS, vol. 99, No. 8, pp. 5400-5405, 2002.
Person et al., "Translation in Micrococcal nuclease-treated cell-free extracts fromehrlich ascites tumor cells", Biochimica et Biophysica Acta., vol. 783, pp. 152-157, 1984.
Pestova et al., "The structure and function of initiation factors in eukaryotic protein synthesis", Cell. Mol. Life Sci., vol. 57, pp. 651-674, 2000.
Preiss et al., "Starting the protein synthesis machine: eukaryotic translation initiation", BioEssays, vol. 25, No. 12, pp. 1201-1211, 2003.
Thoma et al., "A Poly(A) Tail-Responsive In Vitro System for Cap- or IRES-Driven Translation from HeLa Cells", Methods in Molecular Biol., vol. 257, pp. 171-180, 2004, XP002496677.
Morley et al., "A rabbit reticulocyte factor which stimulates protein synthesis in several mammalian cell-free systems", Biochimica et Biophysica Acta, vol. 825, pp. 57-69, 1985.
Bergamini et al., "Picornavirus IRESes and the poly(A) tail jointly promote cap-independent translation in a mammalian cell-free system", RNA, vol. 6, pp. 1781-1790, 2000.
Scheper et al., "Eukaryotic Initiation Factors-4E and -4F Stimulate 5' cap-dependent as Well as Internal Initiation of Protein Synthesis", Journal of Biological Chemistry, vol. 267, No. 11, pp. 7269-7274, 1992.
Scheper et al., "The 5' untranslated region of encephalomyocarditis virus contains a sequence for very efficient binding of eukaryotic initiation factor eIF-2/2B", Biochimica et Biophysica Acta, vol. 1089, pp. 220-226, 1991.
Nevins et al., "Distinct Regulation of Internal Ribosome Entry Site-mediated Translation following Cellular Stress is Medicated by Apoptotic Fragments of eIF4G Translation Initiation Factor Family Members eIF4GI and p97/DAP5/NAT1", Journal of Biological Chemistry, vol. 278, No. 6, pp, 3572-3579, 2003.
Imataka et al., "A newly identified N-terminal amino acid sequence of human eIF4G binds poly(A)-binding protein and functions in poly(A)-dependent translation", EMBO Journal, vol. 17, No. 24, pp. 7480-7489, 1998.
Svitkin et al., "Poly(A)-binding protein interaction with eIF4G stimulates picornavirus IRES-dependent translation", RNA, vol. 7, pp. 1743-1752, 2001.
Imataka et al., "A new translational regulator with homology to eukaryotic translation initiation factor 4G", EMBO Journal, vol. 16, No. 4, pp. 817-825, 1997.
Mikami et al., "An efficient mammalian cell-free translation system supplemented with translation factors", Protein Expression and Purification, vol. 46, pp. 348-357, 2006.
Pelham et al., "An Efficient mRNA-Dependent Translation System from Reticulocyte Lysates", Eur. J. Biochem., vol. 67, pp. 247-256, 1976.
Lee et al., "Enhanced specific antibody productivity of calcium alginate-entrapped hybridoma is cell line-specific", Cytotechnology, vol. 16, pp. 1-15, 1994.
Ishihara et al., "Expression of G protein coupled receptors in a cell-free translational system using detergents and thioredoxin-fusion vectors", Protein Expression and Purification, vol. 41, pp. 27-37, 2005.

(56) References Cited

OTHER PUBLICATIONS

Kalmbach et al., "Functional Cell-free Synthesis of a Seven Helix Membrane Protein: In situ Insertion of a Bacteriorhodopsin into Liposomes", J. Mol. Biol., vol. 371, pp. 639-648, 2007.

Hendrickson, W., "Determination of Macromolecular Structures from Anomalous Diffraction of Synchrotron Radiation", Science, vol. 254, No. 5028, pp. 51-58, 1991.

Spirin et al., "A Continuous Cell-Free Translation System Capable of Producing Polypeptides in High Yield", Science, vol. 242, No. 4882, pp. 1162-1164, 1988.

Kigawa et al., "Structure Determination of Protein Folds Using the Cell-free Synthesis and NMR Spectroscopy", Experimental Medicine, vol. 18, No. 18, pp. 60-64, 2000.

Ge et al., "Simultaneous Introduction of Multiple Mutations Using Overlap Extension PCR", Biotechniques, vol. 22, No. 1, pp. 28 and 30, 1997.

Kigawa et al., "Cell-free synthesis and amino acid-selective stable isotope labeling of proteins for NMR analysis", Journal of Biomolecular NMR, vol. 6, No. 2, pp. 129-134, 1995.

Ikura M., "Heteronuclear 3D NMR and isotopic labeling of calmodulin. Towards the complete assignment of the 1H HRM spectrum", Biochem. Pharrnacol., vol. 40, No. 1, pp. 153-160, 1990.

Patzlaff et al., "An Isotope-edited FT-IR study of a symporter, the lactose permease", Biochem., vol. 41, pp. 7366-7372, 2002.

Ikura et al., "A novel approach for sequential assignement of 1H, 13C, and 15N spectra of proteins: heteronuclear triple resonance three-dimensional NMR spectroscopy. Application to calmodulin.", Biochemistry, vol. 29, pp. 4659-4667, 1990.

Weber et al., "Inhibition of Protein Synthesis by Cl-*", Journal of Biological Chemistry, vol. 252, No. 11, pp. 4007-4010, 1977.

Cooper et al., "Transcription of Vaccinia Virus mRNA Coupled to Translation In Vitro", Virology, vol. 88, No. 1, pp. 149-165, 1978.

Dougherty et al., "Translation of Potyvirus RNA in a Rabbit Reticulocyte Lysate: Reaction Conditions and Identification of Capsid Protein as One of the Products of in Vitro Translation of Tobacco Etch and Pepper Mottle Viral RNAs", Virology, vol. 101, No. 2, pp. 466-474, 1980.

Hardwick et al., "Cell-free protein synthesis by kidney from the aging female fischer F344 rat", Biochimica et Biophysica Acta, vol. 652, No. 1, pp. 204-217, 1981.

Office Action mailed Aug. 10, 2010 in Japanese Application No. 2004-333250.

Mori et al., "Cell-free translation of carbamyl phosphate synthetase I and ornithine transcarbamylase messenger RNAs of rat liver. Effect of dietary protein and fasting of translatable mRNA levels", Journal of Biological Chemistry, vol. 256, No. 8, pp. 4127-4132, 1981.

Cosgrove et al., "Absence of age differences in protein synthesis by rat brain, measured with an initiating cell-free system", Neurobiology of Aging, vol. 8, No. 1, pp. 27-34, 1987.

Bulleid et al., "Cell-free synthesis of enzymically active tissue-type plasminogen activator", Biochem. J., vol. 286 (Part 1), pp. 275-280, 1992.

Emmerich et al., "Characterisation of Protein Synthesis in Cell-Free Extracts from Different Mammalian Cells by their Sensitivity to Inhibitors of Polypeptide-Chain Initiation", Hoppe-Seyler's Z. Physiol. Chem., vol. 360, No. 8, pp. 1099-1111, 1979.

Svitkin et al., "Complete transition of the hepatitis C virus genome in vitro: membranes play a critical role in the maturation of all virus proteins except for NS3", Journal of Virology, vol. 79, No. 11, pp. 6868-6881, 2005.

Evdokimova et al., "The major mRNA-associated protein YB-1 is a potent 5' cap-dependent mRNA stabilizer", The EMBO Journal, vol. 20, No. 19, pp. 5491-5502, 2001.

Kodukula et al., "Biosynthesis of phosphatidylinositol-glycan (PI-G)-anchored membrane proteins in cell-free systems: PI-G is an obligatory cosubstrate for COOH-terminal processing of nascent proteins", Proc. Natl. Acad. Sci., vol. 89, No. 11, pp. 4982-4985, 1992.

Merola et al., "Folding of hepatitis C virus E1 glycoprotein in a cell-free system", Journal of Virology, vol. 75, No. 22, pp. 11205-11217, 2001.

Kigawa, T., "Large-Scale Preparation of Proteins by the Cell-Free Synthesis", Biophysics, vol. 40, No. 6, pp. 391-394, 2000.

Seibutsubutsuri, vol. 40, pp. 391-394 (2000).

Office Action dated Sep. 14, 2010 in JP Patent Appl No. 2004-335514 (partial English translation).

Sigma-Aldrich product catalog page for Polyoxyethylene 23 lauryl ether (Brij 35), (retrieval 2004).

\* cited by examiner

CELL-FREE PROTEIN SYNTHESIS METHOD WITH THE USE OF LINEAR TEMPLATE DNA AND CELL EXTRACT THEREFOR

This application is a continuation of International Application PCT/JP2005/021265, filed on Nov. 18, 2005, and claims priority to Japanese Patent Application No.2004-335514, filed on Nov. 19, 2004, both of which are incorporated herein by reference in their entireties.

TECHNICAL FIELD

The present invention relates to a process for synthesizing a protein using a cell-free protein synthesis system, in particular, a process for synthesizing a protein in a cell-free system using a linear DNA as a template, and a kit therefore.

BACKGROUND ART

Protein synthesis with a cell-free protein synthesis system has been developed not only in a basic study but also in a practical field such as molecular diagnostics and high-throughput discovery of drug target. In recent years, several techniques of drastically increasing the amount of protein synthesis in this system have been explored (Japanese Patent Kokoku Publication No. JP-B-7-110236, Japanese Patent Kokai Publication No. JP-A-4-200390). Accordingly, this system has been utilized in mass production of proteins for structural analysis by X-ray crystallography, Nuclear Magnetic Resonance (NMR) or the like.

As an extract for carrying out the translation reaction, several extracts derived from E. coli, wheat germ, and rabbit reticulocyte are commercially available. In an E. coli extract, it is known that transcription-translation coupled reaction can be used for synthesizing a protein directly from a DNA. For example, a method using an E. coli S30 extract has been systematically developed by Zubay et al. (Geoffrey Zubay, Annual Review of Genetics, 1973, vol. 7, p. 267-287). The S30 extract comprises ribosomes necessary for translation of mRNA, aminoacyl tRNA synthetases, initiation factors (IF), elongation factors (EF) and release factors (RF) of peptide chain synthesis. When a DNA template is used for protein synthesis, a DNA construct, in which a target protein gene is inserted downstream of a strong promoter (generally, a T7 promoter), is added in the system together with a T7 RNA polymerase and four types of ribonucleotides (ATP, GTP, CTP and UTP) to couple both reactions of transcription and translation. Due to the requirement for ATP energy for synthesis of an aminoacyl-tRNA and a translation reaction with mRNA, an energy regeneration system such as a creatine kinase-creatine phosphate system is added to the cell-free system. With the above components, a protein synthesis reaction occurring in cells is reconstructed in vitro.

In the cell-free protein synthesis system using the S30 extract, various factors that influence the protein synthesis yield are known. For example, proteases present in the extract degrade synthesized proteins. In order to minimize the proteolytic degradation, various E. coli strains (for example, E. coli strain B) deficient in OmpT and Lon proteases have been produced.

On the other hand, various nucleases present in the extract degrade a template DNA or its transcription product, mRNA. With respect to the template DNA, the methods of cell-free protein synthesis are roughly classified into two types, one using a circular DNA cloned in a plasmid, λ phage or the like and another using a linear DNA of a PCR product or the like. Generally, a circular DNA is less susceptible to degradation with nucleases, and the protein synthesis yield is high. Nevertheless, in studies of post genomic research in recent years, structures and functions of a large number of proteins have been comprehensively analyzed, and improvement in production of proteins and efficient operation have been essential subjects. Accordingly, a system has been highly demanded in which a large number of linear DNAs are synthesized by PCR amplification with genomic DNA as a template and proteins are synthesized efficiently with a cell-free protein synthesis system using these DNAs.

It has been reported that the linear template DNA is susceptible to degradation with an endogenous exonuclease present in an E. coli extract (Pratt et al., Nucleic Acids Res., 9, 4459-4474, (1981); Benzinger et al., J. Virol., 15, 861-871, (1975); Lorenz and Wackernagel, Microbiol Rev., 58, 563-602, (1994)). It has also been known that since a protein complex called a degradosome recognizes and degrades an RNA, the expression efficiency is decreased. For solving these problems, a freeze-thawing procedure has been conducted as a step of producing an S30 extract to remove the degradosome (WO Pamphlet No. 01/83805), or an E. coli strain in which a mutation is introduced into the rne gene encoding an endonuclease RNase E as an essential component of the degradosome has been produced (for example, a strain BL21-Star, Invitrogen). Regarding the enzyme that degrades a linear DNA, DNA exonucleases such as RecBCD are considered to be a cause of degradation, and various mutant E. coli strains of RecBCD deficient in some of these nucleases have been produced (Yang et al., PNAS 77, 7029-7033 (1980)). However, despite that the degradation activity of linear DNAs in E. coli mutant strains of RecBCD has been decreased, the growth capability of the mutant strains is also lower in many cases. Thus, the strains are not necessarily appropriate for production of an extract for cell-free protein synthesis (Yu et al., PNAS, 97, 5978-5983, (2000)).

SUMMARY OF THE DISCLOSURE

In view of the foregoing problems, it is an object of the present invention to provide a simple and efficient process for synthesizing a large amount of proteins in a cell-free protein synthesis system, by a long-lasting continuous synthesis reaction using a linear DNA as a template.

To solve the foregoing problems, the present inventors have conducted various investigations on a cell-free protein synthesis system using E. coli. Consequently, they have found that, when a synthesis reaction is carried out for a long period of time using a linear DNA as a template, use of an extract prepared from E. coli cells cultured at a low temperature improves and secures a stable yield of the synthesized proteins. In addition, a high synthesis yield is obtained, especially in a continuous reaction such as a dialysis method or a continuous flow method. These findings have led to the completion of the invention.

That is, a process for producing a protein in the present invention comprises conducting a continuous synthesis reaction for at least one hour, preferably from 2 to 8 hours using a cell-free protein synthesis system comprising an extract of E. coli cells cultured at any temperature of from 18° C. to 36° C. and a linear template DNA encoding the protein. The culture temperature of E. coli is preferably from 20° C. to 34° C., more preferably from 26° C. to 32° C. The process for producing the protein in the invention has a feature that it is suitable for a continuous reaction for a long period of time. In particular, the continuous protein synthesis system is preferably a dialysis system or a continuous flow system. A dialysis system for cell-free protein synthesis system comprises an internal dialysate comprising the extract and the linear template DNA, an external dialysate comprising a low-molecular weight substrate for protein synthesis and a dialysis membrane through which the substrate can be transferred.

In another aspect of the invention, there is provided a kit for cell-free protein synthesis using a linear template DNA, comprising an extract of E. coli cells cultured at any temperature of from 18° C. to 36° C. The temperature of culture of the E. coli is preferably from 20° C. to 34° C., more preferably from 26° C. to 32° C.

The meritorious effects of the present invention are summarized as follows.

According to the process of the invention, a large amount of protein can efficiently be synthesized in a continuous reaction system of dialysis or the like using many types of linear double-stranded DNAs as a template, prepared by a method such as PCR. A synthesis amount of protein per se is slightly decreased compared with a case using a circular plasmid DNA. However, many samples can be treated at once without the need of conducting a cloning procedure of template DNAs. Accordingly, the method is appropriate for preparation of samples for high-throughput screening or comprehensive protein analysis.

PREFERRED MODES OF THE INVENTION

In the process of the invention, the cell-free protein synthesis system is a system to synthesize a target protein by preparing a cell extract including protein factors necessary for protein translation, and reconstructing the reaction in vitro. The cell-free system can be constructed using extracts derived from various organisms. For example, extracts of eukaryotic and prokaryotic cells having high protein synthesis activity, such as bacteria including E. coli, thermophilic bacteria and the like, wheat germ, rabbit reticulocyte, mouseL cells, Ehrlich's ascitic cancer cells, Hela cells, CHO cells, budding yeast, and the like (Clemens, M. J., Transcription and Translation—A Practical Approach, (1984), pp. 231-270, Henes, B. D. et al. eds., IRL Press, Oxford).

In the process of the invention, the extract for cell-free protein synthesis suitable for a linear template DNA can be prepared by culturing these eukaryotic or prokaryotic cells at a temperature lower than an optimum growth temperature. For example, since an optimum growth temperature of E. coli is approximately 37° C., E. coli is cultured at any temperature of from 18° C. to 36° C. in the process of the invention. When the temperature is lower than 18° C., the growth rate becomes too slow and such a reaction as low-temperature stress occurs. Further, upon the cultivation of E. coli, it is well known to a skilled person that any growth of E. coli is observed until the temperature is decreased to about 20° C., even though the growth rate is low. Accordingly, the culture of E. coli is conducted preferably at from 20° C. to 34° C., more preferably at from 26° C. to 32° C.

It is speculated that production of proteases and various nucleases in cells is suppressed by culturing E. coli at a low temperature. However, its mechanism is not necessarily clarified. Since growth of cells are regulated by various protein interactions in the cells, it is considered that the culture condition at a low temperature leads not only to suppress the expression of various protease or nuclease proteins per se but also to control activity or expression of these enzymes indirectly via control or increase of expression of other proteins. With respect to the influence on the nuclease functions, the low temperature is considered to inhibit one or both of exonuclease activity of degrading a linear DNA in cells and ribonuclease activity of promoting degradation of an mRNA as a translation product. Further, E. coli is an organism of which genetic analysis has been most progressed, and a large number of mutants have been so far produced. Accordingly, the process of the present invention may have different effects on the protein synthesis depending on the genetic background of E. coli strains used to prepare an extract, while an outstanding effect is observed in at least E. coli strain B, especially strains BL21 and BL21 codon plus. Since the process of the invention is a relatively simple process in which the culture temperature of E. coli is decreased, a synergistic effect can also be obtained in combination with E. coli strains having various genetic mutations.

As an E. coli extract, the S30 extract prepared by the method described in Zubay et al. (supra) or Pratt et al. (Pratt, J. M. et al., Transcription and Translation—A Practical Approach, (1984), pp. 179-209, Henes, B. D. et al. eds., IRL Press, Oxford) can be used. The E. coli S30 extract contains all the enzymes and factors from E. coli required for transcription and translation. Additionally, a supplemental mixture can be added. With respect to a specific method, E. coli is first cultured, and cells are harvested by centrifugation or the like. The harvested cells are washed, then resuspended in a buffer solution, and disrupted with a French press, glass beads, a Waring blender or the like. Insolubles of disrupted E. coli are removed by centrifugation, and the supernatant is then combined with a preincubation mixture, followed by incubation. While this operation degrades the endogenous DNAs and RNAs, it may further include a step of adding a calcium salt or micrococcal nuclease or the like to degrade intrinsic nucleic acids. The extract is then dialyzed to remove endogenous amino acids, nucleic acids, nucleotides and the like, and stored in liquid nitrogen or at −80° C. after dispensing appropriate aliquots.

When a protein synthesis reaction is carried out, the cell extract can be added to a template DNA or RNA for transcription/translation, substrate amino acids, energy sources, various ions, a buffer solution, an ATP regeneration system, a nuclease inhibitor, tRNAs, a reducing agent, polyethyleneglycol, cAMP, folic acids, an antimicrobial agent, substrates for RNA synthesis and RNA polymerase using DNA as a template, and the like. These reaction mixtures are properly selected and prepared in accordance with kinds of target proteins or employed protein synthesis systems. In case of E. coli S30 extract, it is supplemented with all or some of the following: Tris-acetate, dithiothreitol (DTT), NTPs (ATP, CTP, GTP and UTP), phosphoenolpyruvate, pyruvate kinase, at least one amino acid (including 20 natural amino acids and their derivatives. When a protein is labeled with a radioisotope, the remainders except a labeled amino acid are added), polyethylene glycol (PEG), folic acid, cAMP, tRNA, ammonium acetate, potassium acetate, potassium glutamate, an optimum concentration of magnesium acetate and the like. These supplemental solutions are usually stored separately from the S30 extract, and then combined just before use. It is also possible that these are previously mixed with the S30 extract and freeze-thawing is conducted to remove the RNA degradosomes (refer to pamphlet of International Publication No. WO 0183805). The E. coli cell extract prepared by the foregoing method for use in the process of the invention can be dispensed for easy use in aliquots and distributed as a cell-free protein synthesis kit for a linear template DNA. These products can be stored in a frozen or dry state, and put on the market as a kit in suitable containers for storage and shipment. The kit can be accompanied by an instruction manual, a positive control DNA, a vector DNA and the like.

The linear template DNA used in the process of the invention is a double-stranded DNA comprising an appropriate expression control region and a gene sequence encoding a desired protein to be expressed. For increasing expression efficiency of the protein, it is required to promote transcription using a strong promoter or terminator and to increase translation efficiency by increasing affinity between the mRNA and ribosomes. For example, it is known that T7 RNA polymerase derived from T7 phage has quite strong transcriptional activity to produce a recombinant protein at a high level. For increasing translation efficiency, it is further important to introduce a ribosome binding sequence (RBS) which is also called an SD sequence. For quickly purifying or detecting the synthesized protein, it is also possible to design a template DNA for synthesizing a fusion protein having an affinity tag incorporated therein. An improved method for efficiently producing such a linear template DNA is disclosed in a pamphlet of International Publication No. 03004703 by the present Applicant, and the contents thereof are incorporated in this application by reference.

An ordinary known technique such as a batch method or a continuous flow method can be applied to the cell-free protein synthesis system of the invention. The process of the invention is appropriate for a continuous reaction for a long period of time, i.e., a continuous protein synthesis reaction for at least one hour, preferably from 2 to 8 hours. Continuous synthesis for 18 hours or more is enabled by treatment of a reaction system such as exchange of the external dialysate with a fresh one during the synthesis reaction.

[Dialysis Apparatus]

A dialysis apparatus can be used, which comprises an internal dialysate and an external dialysate separated via a dialysis membrane, and is capable of shaking or stirring them. Examples of small-scaled reactors include the Dispo Dialyzer® (manufactured by Spectrum) and the Slidealyzer® (manufactured by Pierce). Further, as a large-scaled reactor, the Spectra/Por® tube for dialysis (manufactured by Spectrum) can be mentioned.

[Internal Dialysate]

An internal dialysate (namely, a protein synthesis reaction solution) in a cell-free protein synthesis system may contain, in addition to a concentrated cell extract of E. coli S30 or the like, a DNA encoding a desired protein, ATP (adenosine 5'-triphosphate), GTP (guanosine 5'-triphosphate), CTP (cytidine 5'-triphosphate), UTP (uridine 5'-triphosphate), a buffer solution, salts, amino acids, an RNase inhibitor, an antimicrobial agent, an RNA polymerase (for example, T7 RNA polymerase), tRNA and the like. Further, it may contain a combination of phosphoenol pyruvate and pyruvate kinase or a combination of creatine phosphate and creatine kinase as an ATP regeneration system, polyethylene glycol (for example, #8000), 3',5'-cAMP, folic acids, an RNase inhibitor, a reducing agent (for example, dithiothreitol) and the like.

[External Dialysate]

On the other hand, an external dialysate (namely, a protein synthesis substrate solution) may be a solution obtained by removing a cell extract, an RNase inhibitor, a DNA or RNA and an RNA polymerase from the internal dialysate. It can contain, for example, a buffer solution, ATP, GTP, CTP, UTP, salts, amino acids and an antimicrobial agent. Concentrations of the components can optionally be selected. As a buffer solution, a buffering solution such as Hepes-KOH or Tris-OAc is available. Examples of salts include acetates (for example, ammonium acetate and magnesium acetate), glutamates and the like. Examples of an antimicrobial agent include sodium azide, ampicillin and the like. Examples of amino acids include 20 types of amino acids constituting proteins.

A closed system consisting of the internal dialysate and the external dialysate at the inside and outside of the dialysis membrane respectively, is shaken or stirred (rotational stirring or the like), whereby substances can be transferred through the membrane depending on the molecular weight limit of the membrane. The synthesized target protein can be recovered from the internal dialysate or external dialysate.

The present invention is now explained in more details by reference to the following Examples using CAT protein, which are not intended to limit the present invention.

EXAMPLES

[Synthesis of CAT Protein Using E. coli S30 Extracts Cultured at Various Temperatures]

E. coli strain BL21 codon plus was cultured for overnight in a typical liquid medium to prepare a seed culture. The seed culture was inoculated into a fermentor containing 7L of 2×YT medium (16 g/l bactotryptone, 10 g/l yeast extract and 5 g/l NaCl), and cultured at each temperature of 30° C., 32° C., 34° C. and 37° C. with sufficient aeration by stirring at 400 rpm. The cell number was estimated using turbidity (absorbance at 600 nm) of the culture solution. The cells were recovered at a later stage of logarithmic growth phase (when absorbance at 600 nm was approximately 3 and the cell number was approximately $10^9$ cells/ml), and E. coli S30 extracts were prepared according to the method of Zubay et al (supra).

As a template DNA in a protein synthesis reaction, both of a plasmid vector for CAT expression, pK7-CAT (refer to Kim et al., Eur. J. Biochem. 239, 881-886, 1996) and a linear double-stranded DNA amplified by PCR using the plasmid as a template were used. In preparing this linear double-stranded DNA, an ordinary polymerase chain reaction (PCR) was conducted in a reaction mixture of the following composition of Table 1 using 5' primer, M13-45Fw:5'-CCAGGGTTTTC-CCAGTCACGAC-3' (SEQ ID NO. 1) and 3' primer, M13Rev:5'-AATTTCACACAGGAAACAGCTATGAC-3' (SEQ ID NO. 2). With respect to the reaction conditions, initial denaturation was conducted at 94° C. for 2 minutes. Then, a cycle of 94° C. for 30 seconds, 53° C. for 30 seconds and 72° C. for 2 minutes was repeated 10 times. Subsequently, a cycle of 94° C. for 30 seconds, 53° C. for 30 seconds and 72° C. for (2 minutes+5 seconds/cycle) was repeated 20 times. Finally, an elongation reaction was conducted once at 72° C. for 5 minutes.

TABLE 1

| | |
|---|---|
| Template DNA (pK7-CAT) | 50 pg |
| 10 x HiFi PCR buffer | 5 μl |
| 5'-primer (10 μM) | 5 μl |
| 3'-primer (10 μM) | 5 μl |
| 2.5 mM dNTPs | 5 μl |
| Expand HiFi DNA polymerase | 0.35 μl |
| adjusted to 50 μl with water | |

(total amount 50 μl scale)

The protein synthesis reactions were carried out by using the above-prepared linear template DNA and the circular plasmid pK7-CAT, respectively. The reaction mixture of the following composition of Table 2 was dialyzed against an external dialysate of the composition of Table 3. The reaction was carried out at 30° C. for 18 hours while conducting sampling. The scales of the reaction were 30 μl of the reaction mixture and 300 μl of the external dialysate. The synthesized CAT protein was quantified according to the method of Shaw et al. (refer to Methods Enzymol. 735-755, 1975). That is, the acetylation reaction of chloramphenicol by CAT was carried out using acetyl coenzyme A and chloramphenicol as substrates, and the product amount of reduced coenzyme A was determined by colorimetric assay using 5,5'-dithiobis-2-nitrobenzoic acid (DNTB). The CAT activity was calculated based on the increase of absorbance at 412 nm at 37° C. per unit time to determine an amount of CAT protein. Incidentally, as a control experiment, a batchwise synthesis reaction was conducted at 37° C. for one hour by changing the composition of Table 2 such that only cysteine among amino acids was 3 mM, sodium azide was not added, T7 RNA polymerase was 133 μg/ml, an E. coli S30 extract was 24% by volume of the reaction mixture and a template DNA was 4μg/ml.

TABLE 2

Composition of a protein synthesis reaction mixture

| Composition | Concentration |
|---|---|
| HEPES-KOH pH 7.5 | 58.0 mM |
| Dithiothreitol (DTT) | 1.8 mM |
| ATP | 1.2 mM |
| CTP, GTP, UTP | 0.8 mM each |
| Creatine phosphate | 80.0 mM |
| Creatine kinase | 0.25 mg/ml |
| Polyethylene glycol 8000 | 4.0% |
| 3',5'-cAMP | 0.64 mM |
| L(-)-5-formyl-5,6,7,8-tetrahydroforic acid | 68 μM |
| E. coli total tRNA | 175 μg/m |
| Potassium glutamate | 200 mM |
| Ammonium acetate | 27 mM |
| Magnesium acetate | 10.7 mM |
| Amino acids (20 types) | 1.5 mM each |
| Sodium azide | 0.05% |
| T7 RNA polymerase | 66.6 μg/ml |
| E. coli S30 extract | 30% by vol. of the reaction mixture |
| Template DNA (expression vector pK7-CAT or linear DNA) | 1 μg/ml |

TABLE 3

Composition of the external dialysate

| Composition | Concentration |
|---|---|
| HEPES-KOH pH 7.5 | 58.0 mM |
| Dithiothreitol (DTT) | 1.8 mM |
| ATP | 1.2 mM |
| CTP, GTP, UTP | 0.8 mM each |

TABLE 3-continued

Composition of the external dialysate

| Composition | Concentration |
|---|---|
| Creatine phosphate | 80.0 mM |
| Polyethylene glycol 8000 | 4.0% |
| 3',5'-cAMP | 0.64 mM |
| L(-)-5-formyl-5,6,7,8-tetrahydroforic acid | 68 μM |
| Potassium glutamate | 200 mM |
| Ammonium acetate | 27 mM |
| Magnesium acetate | 14.9 mM |
| Amino acids (20 types) | 1.5 mM each |
| Sodium azide | 0.05% |
| Tris-phosphate (pH 8.2) | 3 mM |
| Potassium acetate | 18 mM |

Figure 1:
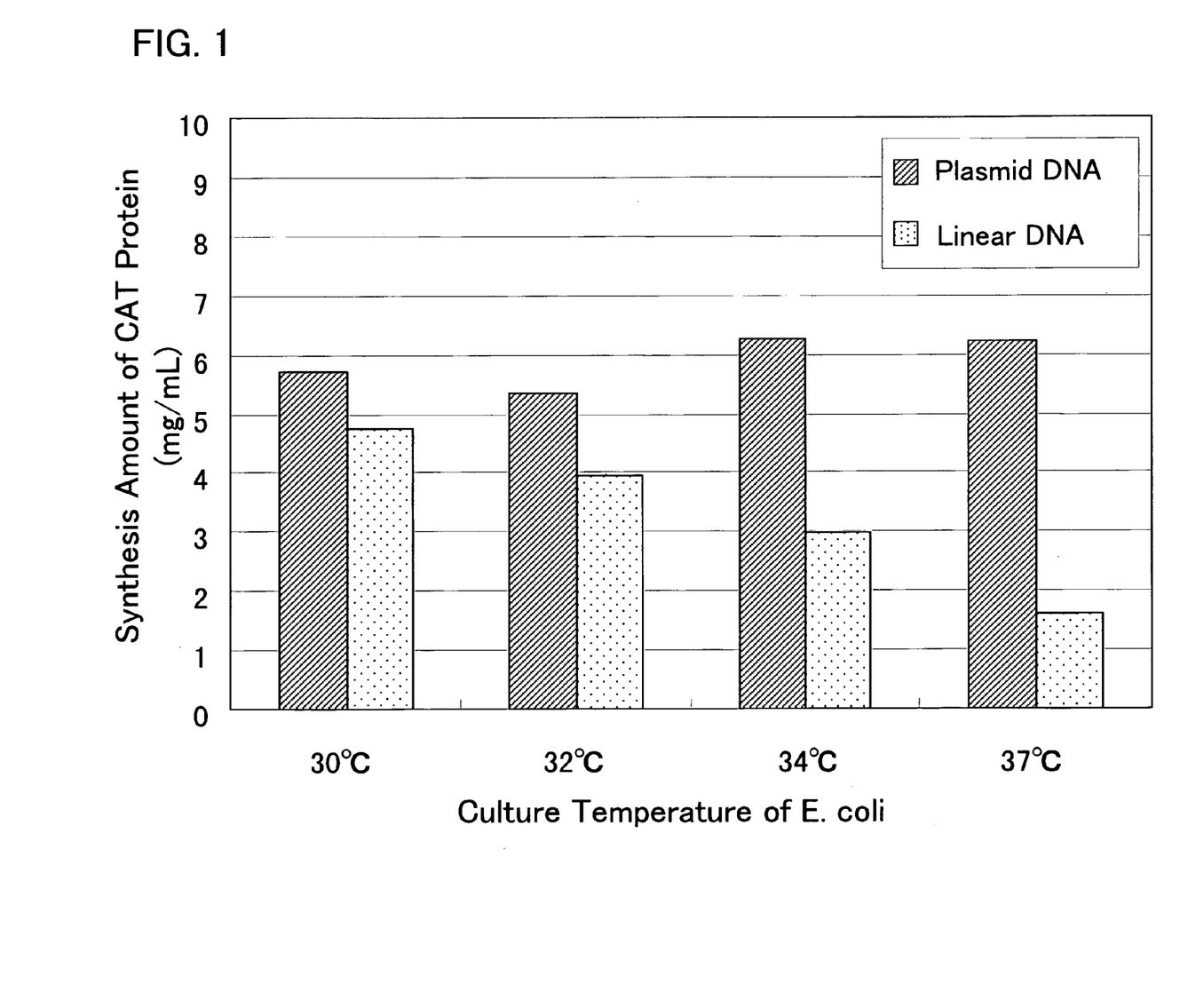
FIG. 1 shows the results provided by conducting a reaction of protein synthesis with a dialysis system at 30° C. for 5 hours using an S30 extract prepared by culturing E. coli strain BL21 codon plus at various temperatures. A synthesis amount of CAT protein was calculated from a measured value of CAT activity.

FIG. 1 shows the results of the quantified protein amounts obtained by measuring CAT activity using a reaction mixture of the synthesis reaction after 5 hours by the dialysis method. Synthesis amounts of the protein using the plasmid DNA as a template were larger at any temperature of from 30° C. to 37° C. than those using the linear template DNA, while the latter cases have a great difference in synthesis amount of the protein depending on the culture temperature of E. coli for preparing the S30 extract. At the culture temperature of 37° C., the synthesis amount of the protein using the linear template DNA was less than one-third that using the plasmid DNA. However, as the culture temperature was decreased, the synthesis amount of the protein was gradually increased. At the culture temperature of 30° C., the synthesis amount of the protein using a linear template was found to be approximately the same as that using the plasmid DNA.

Figure 2:
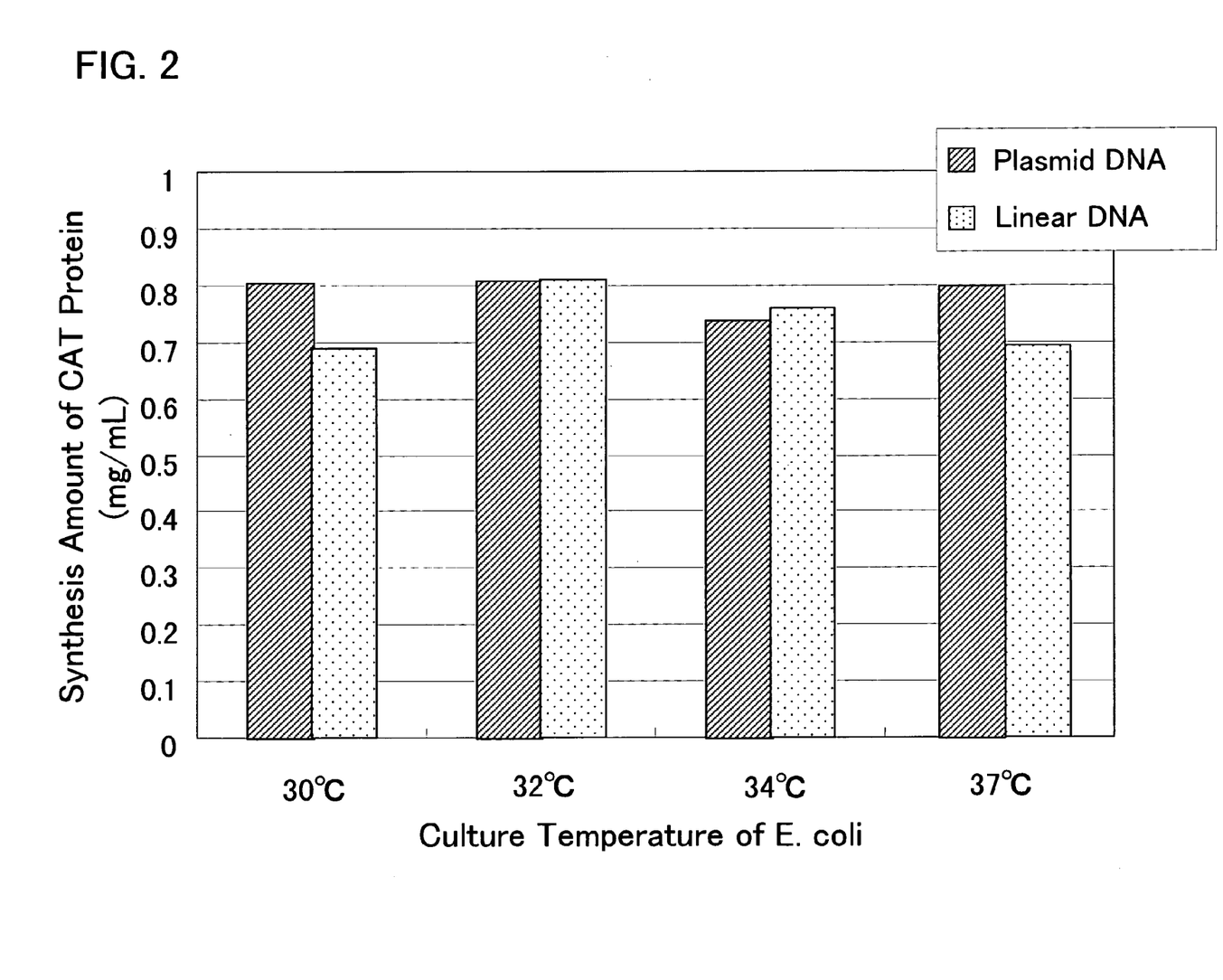
FIG. 2 shows the results provided by conducting a reaction of protein synthesis via a batchwise method at 37° C. for one hour using an S30 extract prepared by culturing E. coli strain BL21 codon plus at various temperatures. A synthesis amount of CAT protein was calculated from a measured value of CAT activity.

Meanwhile, FIG. 2 shows the results of the batchwise protein synthesis conducted as a control experiment. In this reaction condition, the synthesis of the protein has been almost completed at 37° C. for one hour, and there is no great difference in synthesis amount depending on the type of the template DNA. In addition, as is clear from FIG. 2, the synthesis amounts of CAT protein itself are by far lower than those synthesized by the dialysis method.

Figure 3:
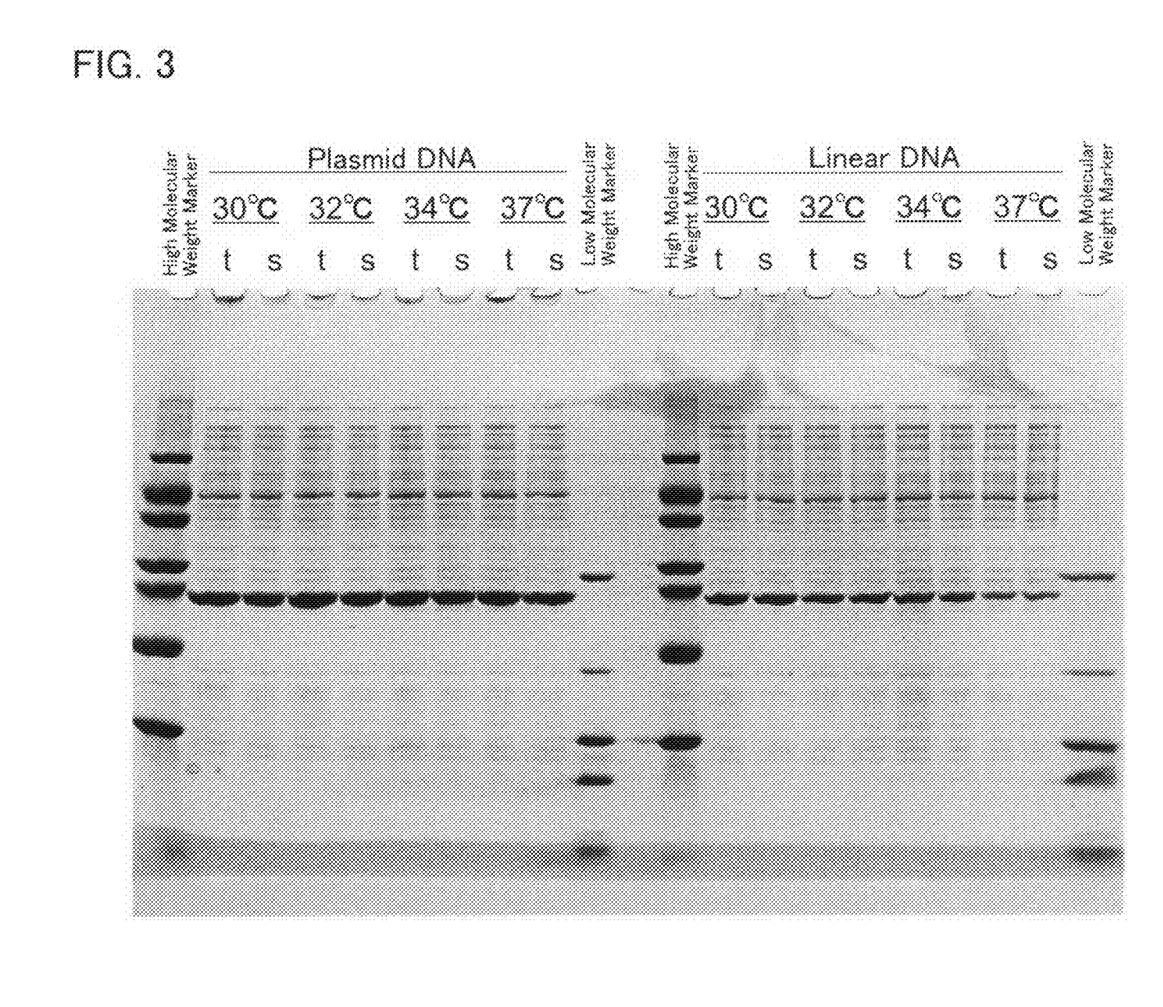
FIG. 3 shows the results obtained by analyzing, via SDS-PAGE, one μl of a reaction solution provided by the protein synthesis reaction with a dialysis system at 30° C. for 18 hours using an S30 extract prepared by culturing E. coli strain BL21 codon plus at various temperatures.

FIG. 3 shows the results of SDS-Polyacrylamide Gel Electrophoresis using 1 μl of the reaction mixture as a sample resulting from the synthesis reaction for 18 hours by the dialysis method. The left half of FIG. 3 shows proteins synthesized at the respective culture temperatures of E. coli using the plasmid DNA as a template, and the right half thereof shows the similar results provided when using the linear DNA as a template. A molecular weight marker was loaded on both ends of the sample. As is apparent from FIG. 3, CAT protein detected around the position of molecular weight 23 kDa was not influenced by the culture temperature of E. coli when using the plasmid DNA. Meanwhile, when using the linear DNA, it was observed that the density of the protein band was increased with decreasing the culture temperature of E. coli. Thus, the results are in good agreement with those shown in FIG. 1 with reproducibility.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

What is claimed is:

1. A process for producing a protein, which comprises conducting a continuous synthesis reaction for at least one hour using a cell-free protein synthesis system which is a dialysis system comprising a) an extract of E. coli cells and b) a linear template DNA encoding the protein wherein the E. coli extract is prepared from E. coli cells exhibiting an exonuclease activity, cultured at any temperature of from 18° C. to 36° C. and recovered at the late-logarithmic phase of culture, and wherein the continuous synthesis reaction is performed without specifically inhibiting DNA exonuclease activity in the protein synthesis reaction.

2. The process according to claim 1, wherein the E. coli cells are cultured at a temperature from 20° C. to 34° C.

3. The process according to claim 1, wherein the dialysis system comprises an internal dialysate comprising the extract and the linear template DNA, an external dialysate comprising a low-molecular weight substrate for protein synthesis and a dialysis membrane through which the substrate can be transferred.

4. The process according to claim 1, wherein the extract is an S30 extract.

5. The process according to claim 1, wherein the linear template DNA is a PCR amplification product.

6. The process according to claim 1, wherein E. coli is a strain BL21 or a strain BL21 codon plus.

7. The process according to claim 1, in which the DNA exonuclease is RecBCD.

8. A process for producing a protein, which comprises conducting a continuous synthesis reaction for at least one hour using a cell-free protein synthesis system which is a dialysis system comprising a) an extract of E. coli cells and b) a linear template DNA encoding the protein wherein the E. coli extract is prepared from E. coli cells exhibiting an exonuclease activity and cultured at any temperature of from 30° C. to 34° C. and wherein the continuous synthesis reaction is performed without specifically inhibiting DNA exonuclease activity in the protein synthesis reaction.

9. The process of claim 8, in which the E. coli cells are cultured at a temperature from 32° C. to 34° C.

10. The process according to claim 8, wherein the E. coli is a strain BL21 or a strain BL21 codon plus.

11. The process according to claim 9, wherein the E. coli is a strain BL21 or a strain BL21 codon plus.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: 5' primer M13-45Fw

<400> SEQUENCE: 1
ccagggtttt cccagtcacg ac                                    22

<210> SEQ ID NO 2
<211> LENGTH: 26
<212> TYPE: DNA
<213> ORGANISM: Artificial Sequence
<220> FEATURE:
<223> OTHER INFORMATION: 3' primer M13Rev

<400> SEQUENCE: 2
aatttcacac aggaaacagc tatgac                                26